US00PP22633P3

(12) United States Plant Patent
Dai et al.

(10) Patent No.: US PP22,633 P3
(45) Date of Patent: Apr. 10, 2012

(54) STRAWBERRY PLANT NAMED 'BARAK'

(50) Latin Name: *Fragaria×ananassa Duch. (Fragaria L.)*
Varietal Denomination: BARAK

(75) Inventors: Nir Dai, Kfar Maas (IL); Zecharia Tanami, Hasmonaim (IL); Sara Slotzky, Or Yehuda (IL); Ahuva Daos, Ganey Hmoshava (IL)

(73) Assignee: State of Israel, Ministry of Agriculture and Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 12/926,091

(22) Filed: Oct. 26, 2010

(65) Prior Publication Data

US 2011/0107483 P1 May 5, 2011

(30) Foreign Application Priority Data

Oct. 29, 2009 (IL) ..... 4223/09

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'BARAK'. This new strawberry plant named 'BARAK' is primarily adapted to the climate and growing conditions of the Sharon coastal plain, at 32° latitude, located in Israel, and is primarily characterized by high quality fruit with an attractive brilliant appearance, regular consistent conical shape, high total soluble solids, long shelf-life and fruit appearing out of the canopy facilitating harvest.

8 Drawing Sheets

Latin name of the genus and species of the plant claimed: *Fragaria×ananassa* Duch. (*Fragaria* L.).

Variety denomination: 'BARAK'.

PRIORITY CLAIM

This application claims priority under 35 U.S.C. § 119(f) of the Israeli Plant Breeders' Rights Application No. 4223/09 filed Oct. 29, 2009.

BACKGROUND OF THE INVENTION

The present invention relates to a new and distinct strawberry variety named 'BARAK'. The variety is botanically known as *Fragaria×ananassa* Duch.

The new strawberry 'BARAK' is a product of a planned breeding program conducted by the inventors, Nir DAI, Zecharia TANAMI, Sara SLOTZKY and Ahuva DAOS in Bet-Dagan, Israel. The objective of the breeding program was to develop high quality fruit with high eating qualities and long shelf life.

This new strawberry 'BARAK' is a result of a controlled cross made by the inventors in 2004, in a greenhouse in Bet-Dagan, Israel. The female or seed parent is the strawberry variety designated 'TAMIR' (U.S. Plant Pat. No. 20,647, granted Jan. 19, 2010, Israel PBR (plant breeders' rights) application No. 4029/07 filed Oct. 04, 2007, European Community PBR application No. 2008/2105 filed 24 Sep. 2008, South Africa PBR application No. PT 5701, filed Jun. 5, 2009). The male or pollen parent is strawberry breeding line designated 'ARO 730', selected in ARO breeding program, Israel. The new strawberry 'BARAK' was observed and selected by the inventors as a single plant within the progeny of the stated cross in April of 2006, in an experimental greenhouse in Bet-Dagan, Israel. After its selection, the new variety was asexually propagated by stolons (runners) in a nursery located in Bet-Dagan, Israel. The new variety 'BARAK' was intensively tested over the following years in a few small trial plots in Moshav Tsofit, Kadima and Qalansawa, Israel. This propagation has demonstrated that the combination of characteristics as herein disclosed for the new cultivar are firmly fixed and retained through successive generations of asexual propagation. The new variety propagates true-to-type.

BRIEF SUMMARY OF THE INVENTION

'BARAK' is primarily adapted to the climate and growing conditions of the Sharon Coastal Plain, at 32° latitude, located in Israel and to similar climatic regions. This region provides suitable growing conditions in autumn with high temperatures that promote initial plant growth and early fruit production, mild winter with moderate temperatures and many sunny days with low humidity, maintaining plant vigor and fruit quality during fruit production months.

The following traits have been repeatedly observed and are determined to be characteristics of 'BARAK', which in combination distinguishes this strawberry plant as a new, unique and distinct variety:

1. Very uniform consistent conical fruit shape and size, without fruit malformation;
2. Excellent fruit firmness with excellent shelf-life;
3. Glossy deep red external color and deep red internal color;
4. Juicy fruit with desirable flavor;
5. Early fruit production from the end of November in Israel;
6. No chilling requirement for flower induction;
7. Moderate plant size with open, globose appearance;
8. Long fruiting trusses makes picking easier;

9. Large number of runners (stolons) production in the propagation nursery;
10. Good field tolerance to Powdery Mildew.

Plants of the new strawberry variety 'BARAK' differs from the female parent 'TAMIR' (U.S. Plant Pat. No. 20,647 granted Jan. 19, 2010, Israel PBR (plant breeders' rights) application No. 4029/07 filed Oct. 4, 2007, European Community PBR application No. 2008/2105 filed 24 Sep. 2008, South Africa PBR application No. PT 5701 filed Jun. 5, 2009) and from the male parent ARO breeding selection 'ARO 730' in the characteristics described in Table 1.

TABLE 1

| Characteristic | 'BARAK' | 'TAMIR' Registered | 'ARO 730' |
|---|---|---|---|
| Average fruit weight (gm) | 21 gram | 22 gram | 22 gram |
| Unevenness of fruit surface | Absent | Absent or very weak | Weak |
| Insertion of achenes | moderately sunken | Level with surface | Level with surface |
| Attitude of calyx | slightly reflexed | Clasping or detached | Clasping or detached |
| Firmness of the fruit | Firm | Firm | Vary firm |
| Plant size | Medium | Medium | Large |
| Average number of stolons | Very many | Few | Many |
| Foliage color (upper surface) | Medium | Medium to dark | Medium to dark |
| Fruit color | Red to dark red | Orange-red | Dark red |
| Vigor | medium to strong | Medium | Strong |
| Inflorescence position relative to foliage | Above | Level with | Level with |

Of the numerous commercial cultivars known to the present inventors, the most similar to the new strawberry variety 'BARAK' is the commercial strawberry variety 'YAEL' (registered for PBR in Israel, no. 1542, September 1996). Plants of the new strawberry variety 'BARAK' differ from plants of strawberry variety 'YAEL' in the characteristics described in Table 2.

TABLE 2

| Characteristic | 'BARAK' | 'YAEL' Registered |
|---|---|---|
| Average fruit weight (gm) | 21 gram | 23 gram |
| Insertion of achenes | moderately sunken | Below surface |
| Attitude of calyx | slightly reflexed | Clasping or detached |
| Firmness of the fruit | Firm | Firm |
| Plant size | Medium | Large |
| Average number of stolons | Very many | Many |
| Fruit color | Red to dark red | Red to dark red |
| Sweetness | Strong | Medium |
| Foliage color | Dark green | Green |
| Inflorescence position relative to foliage | Above | Level with |

For identification, a series of molecular markers have been developed. The genetic polymorphic pattern of two Cleavage Amplified Polymorphic Sequence (CAPS) markers (A. MSR-AluI and B. APX- MluI (Kunihisa et al., 2003) that differ between the new strawberry variety 'BARAK' and the main commercial Israeli strawberry varieties, as well as, other widely known strawberry varieties is shown in FIG. 7.

BRIEF DESCRIPTIONS OF THE PHOTOGRAPHS

The accompanying color photographs illustrate the overall appearance of typical specimens of the new strawberry variety 'BARAK', at various stages of development as true as it is reasonably possible with color reproductions of this type. Color in the photographs may differ slightly from the color value cited in the botanical description which accurately describes the color of 'BARAK'. The depicted plant and plant parts of the new strawberry variety 'BARAK' were taken in Moshav Tsofit and Volcani Center, Bet Dagan, Israel, at the age of 3 months after planting in September.

FIG. 6. Shows the average maximum and minimum temperatures (° C.) and rainfall at the location where observations were made.

Figure 1:
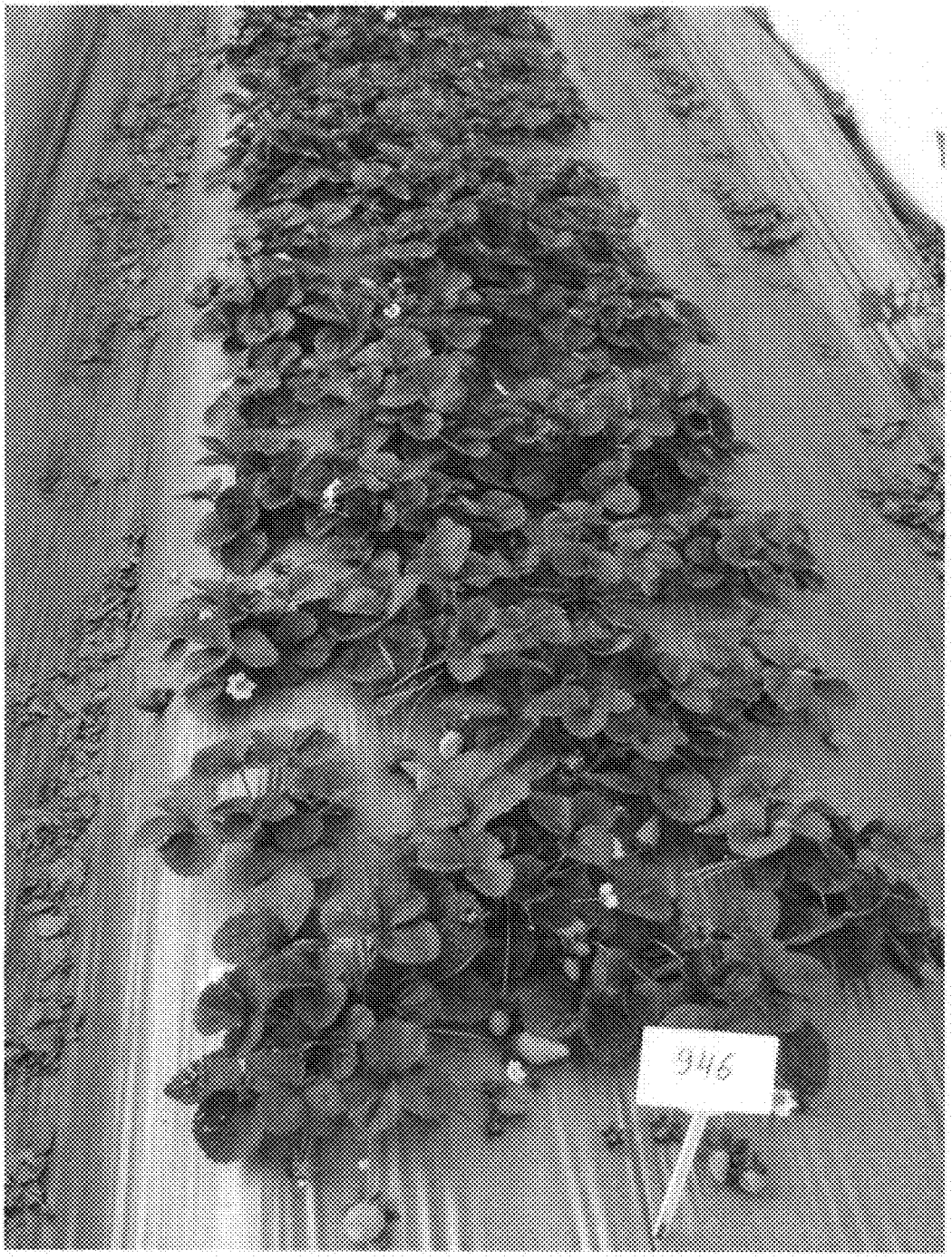
FIG. 1 shows typical fruiting field characteristics of 'BARAK' taken in Moshav Tsofit in January of 2009.
Figure 2A:
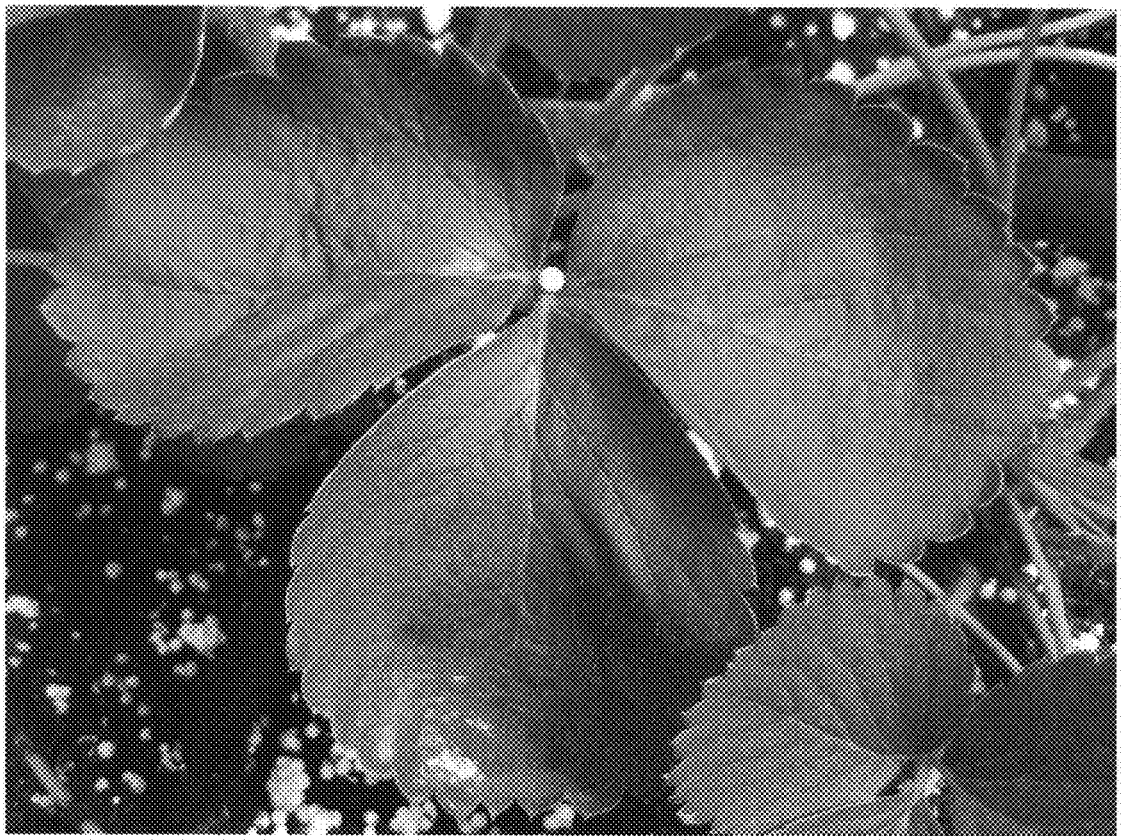
FIG. 2A shows a close-up view of the typical leaf of 'BARAK' taken in Volcani Center, Bet Dagan in June of 2010.
Figure 2B:
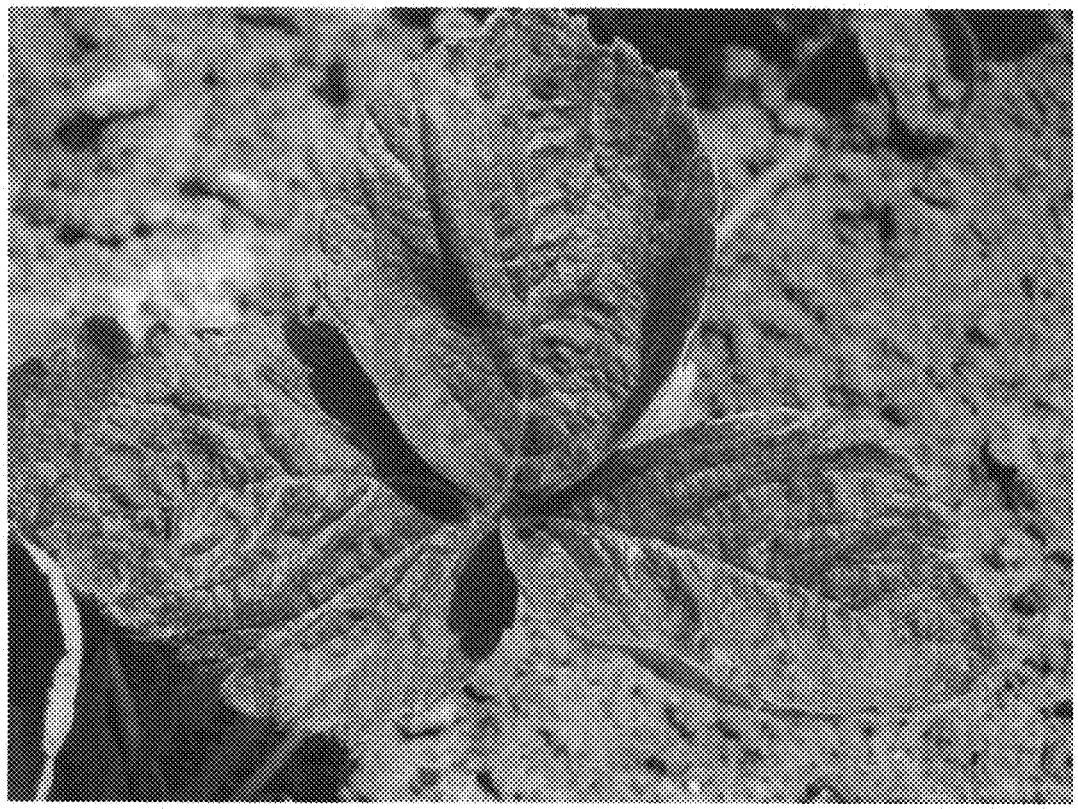
FIG. 2B shows unique heat sensitivity symptoms of 'BARAK' leaves, at high temperatures during the Israeli summer (July-September) taken in Moshav Tsofit in July of 2010.
Figure 3:
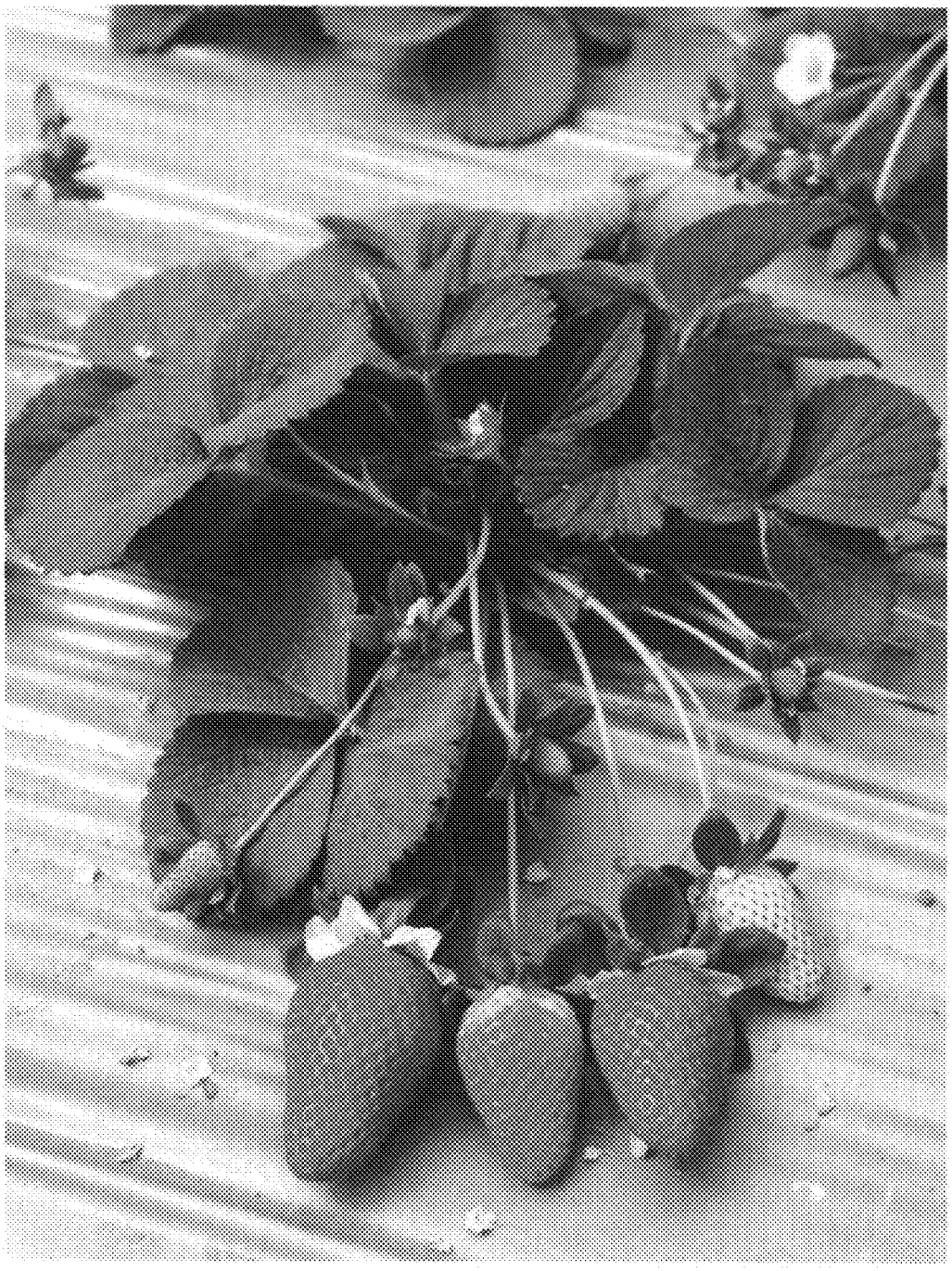
FIG. 3 shows typical mature and immature fruit of 'BARAK' taken in Moshav Tsofit in March of 2009.
Figure 4:
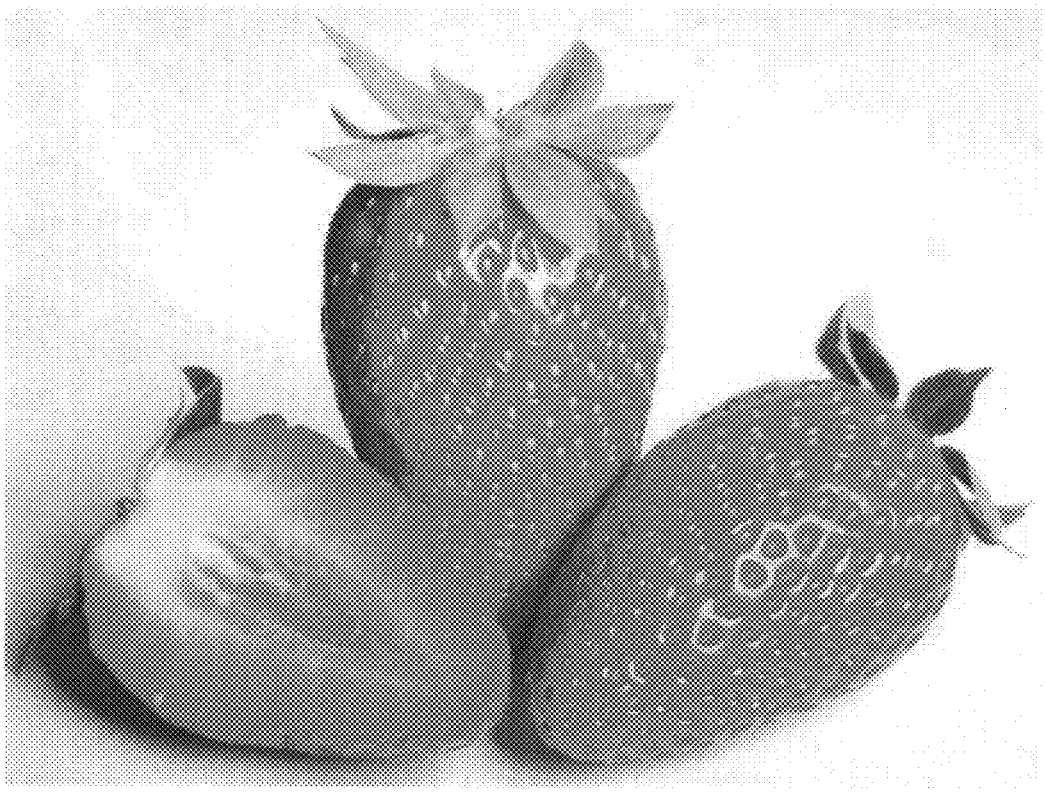
FIG. 4 shows a close-up external and internal view of mature fruit of 'BARAK' taken in Moshav Tsofit in March of 2009.
Figure 5:
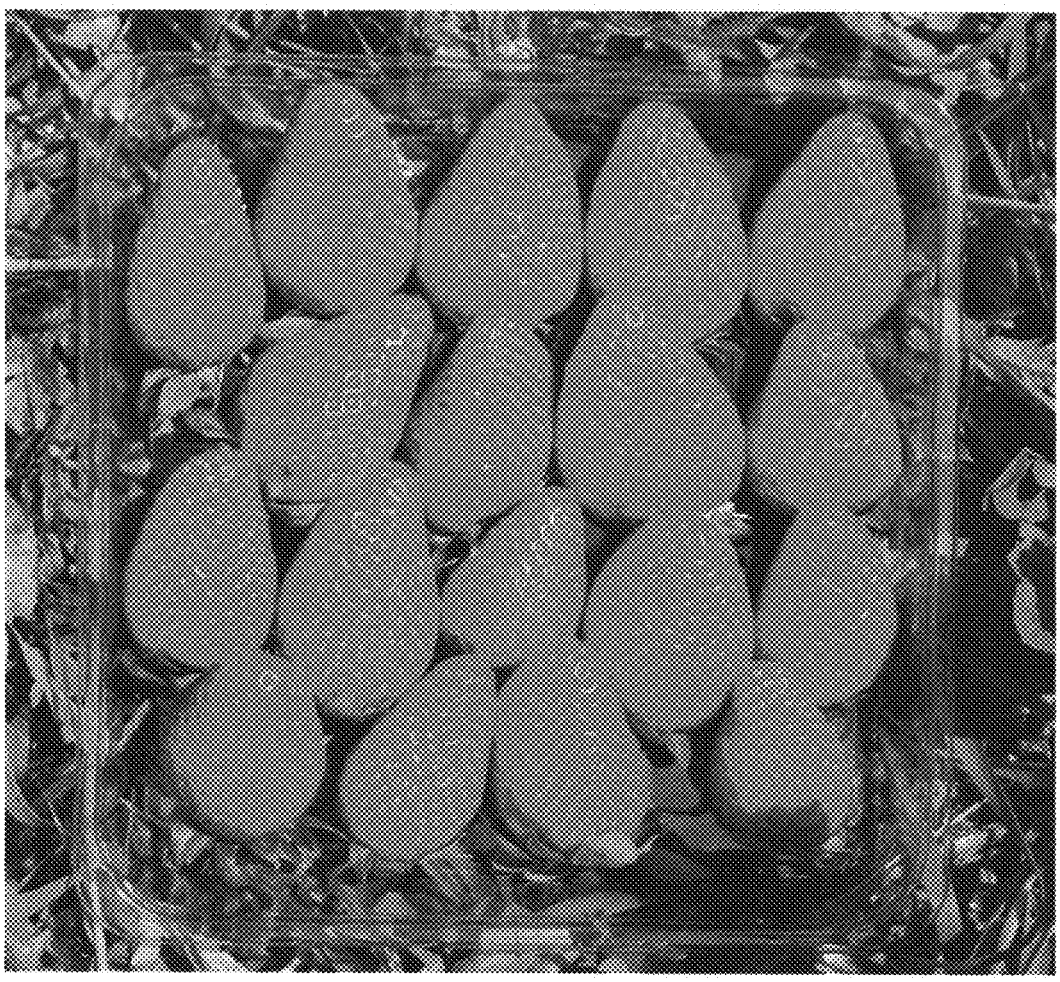
FIG. 5 shows typical fruit shape and other characteristics of 'BARAK' taken in Moshav Tsofit in March of 2009.
Figure 7:
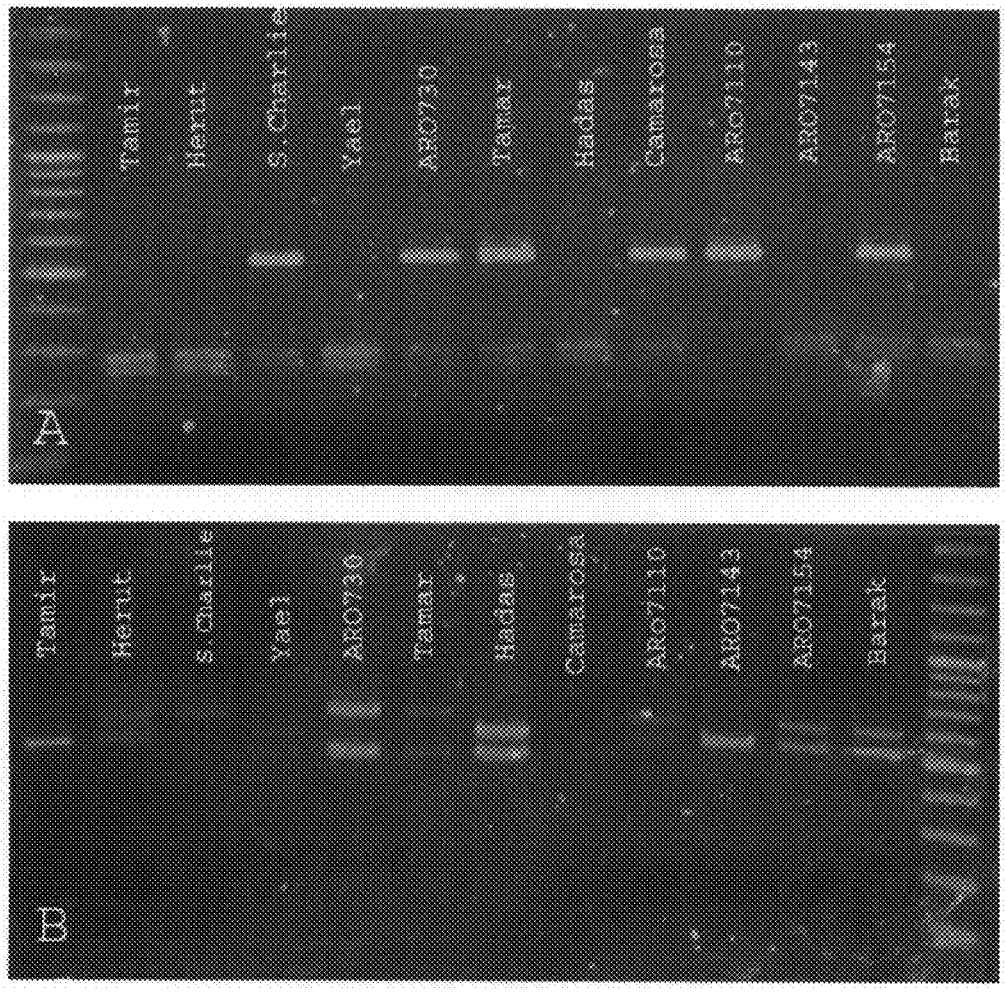

FIG. 7. Shows the genetic polymorphic pattern of 'BARAK' (right line) in comparison to 11 other strawberry accessions at two CAPS markers: A. MSR-AluI and B. APX-MluI, (following Kunisha et al, 2003).

DETAILED BOTANICAL DESCRIPTION

'BARAK' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'BARAK', unless otherwise noted, taken during the winter of the growing season 2008-2009 in Moshav Tsofit Israel. The observations, measurements and values were taken from plants of 'BARAK' dug from a low-elevation nursery located in Moshav Tsofit, Israel, during September, 2008 and planted directly, without any chilling, on the same day, in the field in Moshav Tsofit, Israel. Plants of the new strawberry variety 'BARAK' were grown under conditions which closely approximate those generally used in commercial practice.

Growing conditions at the nursery:

Mother plants provided from an authorized nursery are planted in the beginning of May, in the nursery at 2.5 m×2.5 m distance. Combination of overhead and drip irrigation with addition of fertilizers is used. The average day/night temperatures during the establishment of the daughter plants, between June to August, are 29° C./22° C. Runners appear from June, which produce young daughter plants up till mid September. These are then collected and planted directly in the field.

Growing conditions at the fruit production field as is typically used in agricultural practice.

The plants are washed from soil and dipped in Octav (Prochloraz manganese) 2 g/Liter solution to avoid anthracnose. These bare rooted plants are then planted in raised beds with overhead irrigation in 4 rows at 30 cm apart. Distance between plants within rows is 32 cm. During the first month, no fertilizers are added, due to the addition of 60-100 $m^3$/hectare compost during field preparation. About 4 weeks after planting the beds are covered with silvery-black, 30 micron polyethylene. The young plants are pulled out through the pre-prepared holes. From this point on, the plants are irrigated with a drip system with a supply of additional fertilizers, as is typically used in agricultural practice. By the end of October the beds are covered with transparent, 80 micron thick polyethylene tunnels. The average day (max) and night (minimum) temperatures during the cultivation season are shown in FIG. 6.

During winter in Israel, most days have full sunlight and only an average of 82 rainy days from August to June, producing about 520 mm precipitation. The fields are not treated with growth regulators and regularly are irrigated and fertilized according to need during fruit production.

Yield observations and fruit quality characteristics are averaged from 2 years of data collected from the 2008 to 2009 and 2009 to 2010 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.) (year of edition 1986), except where general colors of ordinary significance are used. Color values were taken under daylight conditions between 10:00 a.m. to noon in Bet-Dagan, Israel. The approximate age of the observed plants is 4 to 6 months.

The following Tables 3 to 9 describe fruit, plant, stolon, foliage, fruiting truss, flower and pest/disease characteristics of the new strawberry 'BARAK'.

TABLE 3

| FRUIT CHARACTERISTICS | |
|---|---|
| Characteristic | 'BARAK' |
| Difference in shapes between primary and secondary flowers | Slight |
| Length | 55-67 mm |
| Maximum diameter | 34-41 mm |
| Ratio of length/maximum width | Much longer than broad |
| Weight | 19-24 g, 21 g average |
| Size | Medium to large |
| Predominant shape | Conical |
| Primary secondary and tertiary fruit | No difference in shape for all three positions |
| Band without achenes | Medium broad (not medium to broad) |
| Unevenness of surface | Even |
| Color | Dark red RHS 45 A |
| Evenness of color | Even |
| Glossiness | Strong |
| Insertion of achenes | Moderately sunken |
| Insertion of calyx | At level |
| Color of achenes | Light yellow green RHS 145 B |
| Density of achenes | Medium to dense |
| Weight of achenes | Not recoded |
| Number of achenes | Number 280-420 |
| Pose of the calyx segments | Slightly reflexed |
| Size of calyx in relation to fruit diameter | Larger |
| Length of calyx segment | 24-30 mm |
| Width of calyx segment | 14-18 mm |
| Color of upper side of calyx segment | Light green 137 C |
| Color of lower side of calyx segment | Dark green RHS 137 A |
| Adherence of calyx | Very strong |
| Firmness | Firm |

TABLE 3-continued

| FRUIT CHARACTERISTICS | |
|---|---|
| Color of flesh | Medium red RHS 45 C |
| Evenness of color of flesh | Even |
| Sweetness | Strong |
| Acidity | Weak |
| Marketable yield (gm/pit) | Monthly yield |

| | Year analyzed: | |
|---|---|---|
| | 2008-2009 | 2009-2010 |
| November | 8 gram/plant | 29 gram/plant |
| December | 143 gram/plant | 48 gram/plant |
| January | 130 gram/plant | 145 gram/plant |
| February | 246 gram/plant | 309 gram/plant |
| March | 217gram/plant | 245 gram/plant |
| Total: | 744 gram/plant | 776 gram/plant |

TABLE 4

| PLANT CHARACTERISTICS | |
|---|---|
| Characteristic | 'BARAK' |
| Habit | Globose |
| Height | About 35 cm |
| Diameter | About 40-45 cm |
| Density | Medium |
| Vigor | Medium to strong |
| Time of flowering | Early |
| Time of ripening | Early |
| Type of bearing | Partly remontant |

TABLE 5

| STOLON CHARACTERISTICS | |
|---|---|
| Characteristic | 'BARAK' |
| Number | Numerous |
| Anthocyanin coloration | Weak |
| Thickness | 2-4 mm |
| Pubescence | Medium to strong |
| Green color | Light green RHS 144 C |

TABLE 6

| FOLIAGE CHARACTERISTICS | | |
|---|---|---|
| | Characteristic | 'BARAK' |
| Leaf | Green color of upper side | Dark RHS 137 A |
| | Green color of lower side | Grey green RHS 138 B |
| | Length | 20-24 cm |
| | Width | 14-16 cm |
| | Cross section | Concave |
| | Blistering | Medium |
| | Number of leaflets | Sometimes more than three |
| Terminal leaflet | Length | 7-9 cm |
| | Width | 7-9 cm |
| | Ratio length/width | As long as broad |
| | Shape of base | Rounded |
| | Shape of teeth | Rounded |
| Side leaflet | Length | 7-8.5 cm |
| | Width | 7-10 cm |
| | Ratio length/width | Broader than long |
| | Shape of base | Right angle |
| Petiole | Pose of hairs | Outwards |
| | Length | 9-17 cm |

TABLE 6-continued

| FOLIAGE CHARACTERISTICS | | |
|---|---|---|
| | Characteristic | 'BARAK' |
| | Thickness | About 3 mm |
| | Green color | Yellow green RHS 144 C |
| | Anthocyanin coloration | Absent or very weak |
| Stipule | Length | 18-25 mm |
| | Width | 5-8 mm |
| | Anthocyanin coloration | Absent or very weak |
| | Green color | Light yellow green RHS 144 D inner and outer side |

TABLE 7

| FRUITING TRUSS CHARACTERISTICS | |
|---|---|
| Characteristic | 'BARAK' |
| Attitude | Prostrate |
| Thickness | 2-3 mm |
| Green color | Yellow green RHS 144 C |
| Pubescence | Medium dense |

TABLE 8

| FLOWER CHARACTERISTICS | | |
|---|---|---|
| | Characteristic | 'BARAK' |
| Inflorescence | Position relative to foliage | Above |
| | Attitude | Prostrate |
| Flower | Diameter | 32-36 mm |
| | Size of calyx relative to corolla | Same size |
| | Size of inner calyx relative to outer calyx | Smaller |
| | Spacing of petals | Touching |
| | Length of sepal | 13-18 mm |
| | Width of sepal | 9-13 mm |
| | Green color of upper side of sepal | Light green 137 C |
| | Green color of lower side of outer whorl of sepal | Medium green RHS 138 B |
| flower base | Pubescence | Strongly pubescent |
| flower base | Color | Yellow green RHS 1 A |
| Petal | Length | 11-15 mm |
| | Width | 12-15 mm |

TABLE 8-continued

| FLOWER CHARACTERISTICS | |
|---|---|
| Characteristic | 'BARAK' |
| Shape | Broader than long |
| Color of upper side | White RHS 155 A |
| Color of lower side | White RHS 155 A |

TABLE 9

| REPRODUCTIVE ORGANS | | |
|---|---|---|
| | Characteristic | 'BARAK' |
| Stamen | Number per flower | Numerous |
| | Length | About 2-4 mm |
| Filament | Length | About 2-4 mm |
| | Color | Light yellow green RHS 145 C |
| Anther | Length | About 0.1 mm |
| Pollen | Amount | Moderate |
| | Color | Dark yellow RHS 14 A |
| Pistils | Number per flower | Numerous |
| | Shape | Too small to observe |
| | Length | Too small to observe |
| Stigma | Length | Too small to observe |
| | Color | Too small to observe |
| Style | Color | Too small to observe |

TABLE 10

| PEST AND DISEASE REACTIONS | |
|---|---|
| Characteristic | 'BARAK' |
| Two spotted spider mite | No testing/observations |
| Lygus bug | No testing/observations |
| Flower thrips | No testing/observations |
| Powdery mildew | moderately tolerant |
| Botrytis fruit rot | moderately tolerant |
| Angular leaf spot | No testing/observations |

We claim:

1. A new and distinct strawberry variety named 'BARAK', as illustrated and described herein.

* * * * *

FIG. 6

Tel Aviv Station height: 4 meters above sea level

| Elements | Jan | Feb | March | Apr | May | Jun | July | Aug | Sep | Oct | Nov | Dec |
|---|---|---|---|---|---|---|---|---|---|---|---|---|
| Mean maximum air temperature (deg C) | 17.5 | 17.7 | 19.2 | 22.8 | 24.9 | 27.5 | 29.4 | 30.2 | 29.4 | 27.3 | 23.4 | 19.2 |
| Mean minimum air temperature (deg C) | 9.6 | 9.8 | 11.5 | 14.4 | 17.3 | 20.6 | 23 | 23.7 | 22.5 | 19.1 | 14.6 | 11.2 |
| Mean rainfall (mm) | 126.9 | 90.1 | 60.6 | 18 | 2.3 | - | - | - | 0.4 | 26.3 | 79.3 | 126.4 |